(12) United States Patent
Schindlbeck et al.

(10) Patent No.: US 11,607,623 B2
(45) Date of Patent: Mar. 21, 2023

(54) DYNAMIC INTERFACE SYSTEM AND ITS APPLICATION IN SUPERCRITICAL FLUID EXTRACTION AND CHROMATOGRAPHY

(71) Applicant: CORNERSTONE TECHNOLOGIES LLC, Louisville, KY (US)

(72) Inventors: Zachariah J. G. X. Schindlbeck, Paris, TN (US); Jeremy Michael Ebersole, Beloit, WI (US); Laurence Bernard Woznicki, Chicago, IL (US)

(73) Assignee: CORNERSTONE TECHNOLOGIES LLC, Louisville, KY (US)

( * ) Notice: Subject to any disclaimer, the term of this patent is extended or adjusted under 35 U.S.C. 154(b) by 404 days.

(21) Appl. No.: 16/989,078

(22) Filed: Aug. 10, 2020

(65) Prior Publication Data
US 2021/0039013 A1 Feb. 11, 2021

Related U.S. Application Data

(60) Provisional application No. 62/884,193, filed on Aug. 8, 2019.

(51) Int. Cl.
| | | |
|---|---|---|
| *B01D 15/14* | (2006.01) | |
| *C07D 311/80* | (2006.01) | |
| *C07C 37/82* | (2006.01) | |
| *C07C 51/47* | (2006.01) | |
| *B01D 15/40* | (2006.01) | |
| *B01D 11/02* | (2006.01) | |
| *B01D 15/16* | (2006.01) | |

(52) U.S. Cl.
CPC .......... *B01D 15/14* (2013.01); *B01D 11/0203* (2013.01); *B01D 11/028* (2013.01); *B01D 11/0292* (2013.01); *B01D 15/161* (2013.01); *B01D 15/163* (2013.01); *B01D 15/40* (2013.01); *C07C 37/82* (2013.01); *C07C 51/47* (2013.01); *C07D 311/80* (2013.01)

(58) Field of Classification Search
CPC .................................................... B01D 15/14
USPC ........................................................ 549/390
See application file for complete search history.

(56) References Cited

U.S. PATENT DOCUMENTS

| 5,750,709 A | 5/1998 | Castor |
| 2006/0247455 A1 | 11/2006 | Krumbholz et al. |
| 2008/0103193 A1 | 5/2008 | Castor et al. |
| 2011/0015418 A1 | 1/2011 | Krumbholz et al. |
| 2015/0126602 A1 | 5/2015 | Bannenberg et al. |
| 2019/0134122 A1 | 5/2019 | Pertile et al. |
| 2019/0184327 A1 | 6/2019 | Wikfors et al. |

FOREIGN PATENT DOCUMENTS

| CN | 105505565 | 4/2016 |
| WO | 2019/032609 | 2/2019 |

OTHER PUBLICATIONS

Sample Injection—Valco 6 port valve—Position A.
Sample Injection—Valco 6 port valve—Position B.

*Primary Examiner* — Taofiq A Solola

(57) ABSTRACT

The present invention provides a dynamic interface system between an extraction device and a chromatographic purification device for separating and purifying substance(s) from a mixture or matrix. One embodiment is the Supercritical Fluid Interface ("SFI") between Supercritical Fluid Extraction ("SFE"), and Supercritical Fluid Chromatography ("SFC"). The SFI is capable of interfacing; gas, subcritical and supercritical fluid extraction methods and pair with gas, subcritical and supercritical fluid chromatography technologies that operate within the pressure and temperature parameters of the SFI. The SFI can operate up to 200 degrees celsius and 5000 psi. This interface technology allows for an inline oil extraction and chromatographic separation, the SFI can pair extraction and chromatography with the same solvent in different mobile phases, whereas the extraction can be performed using $CO_2$ as a solvent in sub-critical phase and the SFI can receive the subcritical solution and then increase pressure and/or temperature to achieve supercritical state as required for injection into supercritical fluid chromatography technologies. The SFI coupling between SFE and SFC can to extract and refine cannabinoids from the *cannabis* industrious, hemp, plant and can also be applied to improve efficiency in an industry that extracts and refines oils, through chromatography, from organic materials using a gas, or sub/supercritical fluid as a solvent and mobile phase.

23 Claims, 5 Drawing Sheets

DYNAMIC INTERFACE SYSTEM AND ITS APPLICATION IN SUPERCRITICAL FLUID EXTRACTION AND CHROMATOGRAPHY

RELATED APPLICATION

The present application claims priority under 35 U.S.C. § 119 to U.S. Provisional Application Ser. No. 62/884,193, filed Aug. 8, 2019, entitled "A Supercritical Fluid Interface Connecting Supercritical Fluid Extraction with Supercritical Fluid Chromatography and Its Application Thereof", which is incorporated herein by reference in their entirety for all purposes.

FIELD OF INVENTION

The present invention generally relates to systems and methods of separating and purifying substance(s) from a mixture or matrix containing the substance(s), and in particular relates to a dynamic interface system between an extraction device and a chromatographic purification device.

DESCRIPTION OF THE RELATED ART

Separating and purifying substance(s) from a mixture or matrix containing the substance(s) is important in scientific research and various industries. Extraction and chromatography are two of the widely used technologies in separation and purification. A supercritical fluid is any substance at a temperature and pressure above its critical point, where distinct liquid and gas phases do not exist. It can diffuse into solids like a gas, and dissolve materials like a liquid.

Supercritical Fluid Extraction (SFE) is the process of separating one or more component (the extractant) from another (the matrix or mixture) using supercritical fluids, at certain temperatures and pressures, as the extracting solvent. Extraction is usually from a solid matrix (like plant material) but can also be from liquids. SFE is used on a large scale to either strip unwanted material from a product (e.g. decaffeination) or collect a desired product (e.g. essential oils). Carbon dioxide ("$CO_2$") is the most used supercritical fluid, sometimes modified by co-solvents such as ethanol or methanol.

Chromatography is the collective term for a set of laboratory techniques for the separation of mixtures. The mixture is dissolved in a fluid called the mobile phase, which carries it through a structure holding another material called the stationary phase. The various constituents of the mixture travel at different speeds, causing them to separate. The separation is based on differential partitioning between the mobile and stationary phases. Subtle differences in a compound's partition coefficient result in differential retention on the stationary phase and thus affect the separation. Supercritical Fluid Chromatography (SFC) is a form of chromatography used for the separation, identification and quantification of certain compounds. SFC is commonly used for purifications in the pharmaceutical industry. It utilizes $CO_2$ as the mobile phase. Therefore, the entire chromatographic flow path must be pressurized. In a supercritical state, $CO_2$ becomes super solvent, which has higher penetration power, and can be fine-tuned to focus in on specific constitutes, by varying the pressure, temperature, and by the use of co-solvents. Through this process, a desired product (e.g. essential oils) can be broken down into more defined individual compounds or recombined to precise concentrations.

While there are many SFE and SFC equipment options available, it is not known of the existence of any dynamic coupling systems of the two technologies, or dynamic coupling of extraction technology and chromatography in general. Current coupling mechanisms do not provide dynamic coupling interaction between the SFE and SFC. The product of the SFE process must be depressurized, combined with various solutions, and re-pressurized for the SFC process. There is not dynamic coupling of the SFE and SFC allowing for direct transfers of supercritical solution from the SFE into the SFC equipment. This cannot be accomplished by existing coupling methods or equipment.

SUMMARY OF THE INVENTION

A dynamic interface system according to the present invention is a novel technology designed to directly couple an extraction device with a chromatographic purification device and eliminate the depressurization-dissolution-repressurization steps currently required for the transition between these two technologies. Dynamic flexibility of the dynamic interface system platform allows for the coupling of an extraction device and chromatographic purification device in a continuous arrangement.

The dynamic interface system according to the present invention serves two basic functions. First, it collects and holds extract-laden products in a solubilized supercritical state. Second, it serves as an injection device allowing for metered introductions of the extracted products into the chromatographic purification device.

The dynamic interface system according to the present invention is positioned between an extraction device and a chromatographic purification device. The dynamic interface system includes a container having an inlet and an outlet connecting with the extraction device and the chromatography device, respectively, a piston in the container and dividing the container into a first compartment and a second compartment, a pressure adjustment device, and a temperature adjustment device. The dynamic interface system may further include a temperature sensor and a pressure sensor. The inlet and outlet connect with the first compartment of the container. There are valves that can open and close the inlet and outlet. The pressure adjustment device communicates with the second compartment of the container to increase or decrease the pressure in the second compartment. The pressure adjustment device can be a compressor pump with gas or hydraulic power or other means. A control device may be provided to control opening and closing of the inlet, the outlet and the temperature and pressure.

The extraction device is a supercritical fluid extraction device and the chromatographic purification device is a supercritical fluid chromatography device. Carbon dioxide may be used as a solvent.

The present invention further provides a separation and purification system including an extraction device; a chromatographic purification device; and a dynamic interface system between the extraction device and the chromatographic purification device as described above.

The present invention additional provides a separation and purification method for separating at least one substance from a mixture or matrix comprising the steps of: treating the mixture or matrix with a solvent under a first pressure and a first temperature in an extraction device; outputting the mixture to a container under a second pressure and a second temperature; outputting the mixture to a chromatographic purification device, where the substance is being separated; and collecting the separated substance.

In the case of selective extraction, the first pressure equals to the second pressure; and the first temperature equals to the second temperature.

The solvent can be a liquid solvent, a gaseous solvent, a subcritical fluid solvent or a supercritical fluid solvent.

In particularly, the present invention provides a solution where the solvent is carbon dioxide and the first and second temperatures and pressures are such that the carbon dioxide is kept at a super critical state.

In one embodiment, the separation and purification method of the present invention is used to process *cannabis* plant materials to extract, separate and purify the substance(s) selected from the group of delta-9-tetrahydrocannabinol (THC), tetrahydrocannabinolic acid (THCA), cannabidiol (CBD), cannabinol (CBN), cannabidiolic acid (CBNA), cannabigerol (CBG) and cannabigerolic acid (CBGA).

In particularly, the dynamic interface system is a Supercritical Fluid Interface (SFI) coupling a Supercritical Fluid extraction (SFE) device with a Supercritical Fluid Chromatography (SFC) unit and related method of extraction and separation. The SFI maintains the supercritical states of the received extractants in its chamber and injecting the extractants to the Supercritical Fluid Chromatography unit for separation and purification. The supercritical fluid can be carbon dioxide and may also include additional co-solvent(s), such as water, ethanol, methanol, etc. Such SFI can be used in obtaining purified *cannabis* compounds from plant materials. It additionally may be used for obtain purified compounds from mixture sources and may be used in food processing, cosmetic, pharmaceutical, agricultural fields.

BRIEF DESCRIPTION OF THE DRAWINGS

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention. In the figures.

DETAILED DESCRIPTION OF THE INVENTION

The dynamic interface system of the present invention can be connected with various extraction technologies and chromatographic purification technologies to provide a versatile solution for separating and purifying substance(s) from a mixture or matrix containing the substance(s).

Figure 1:
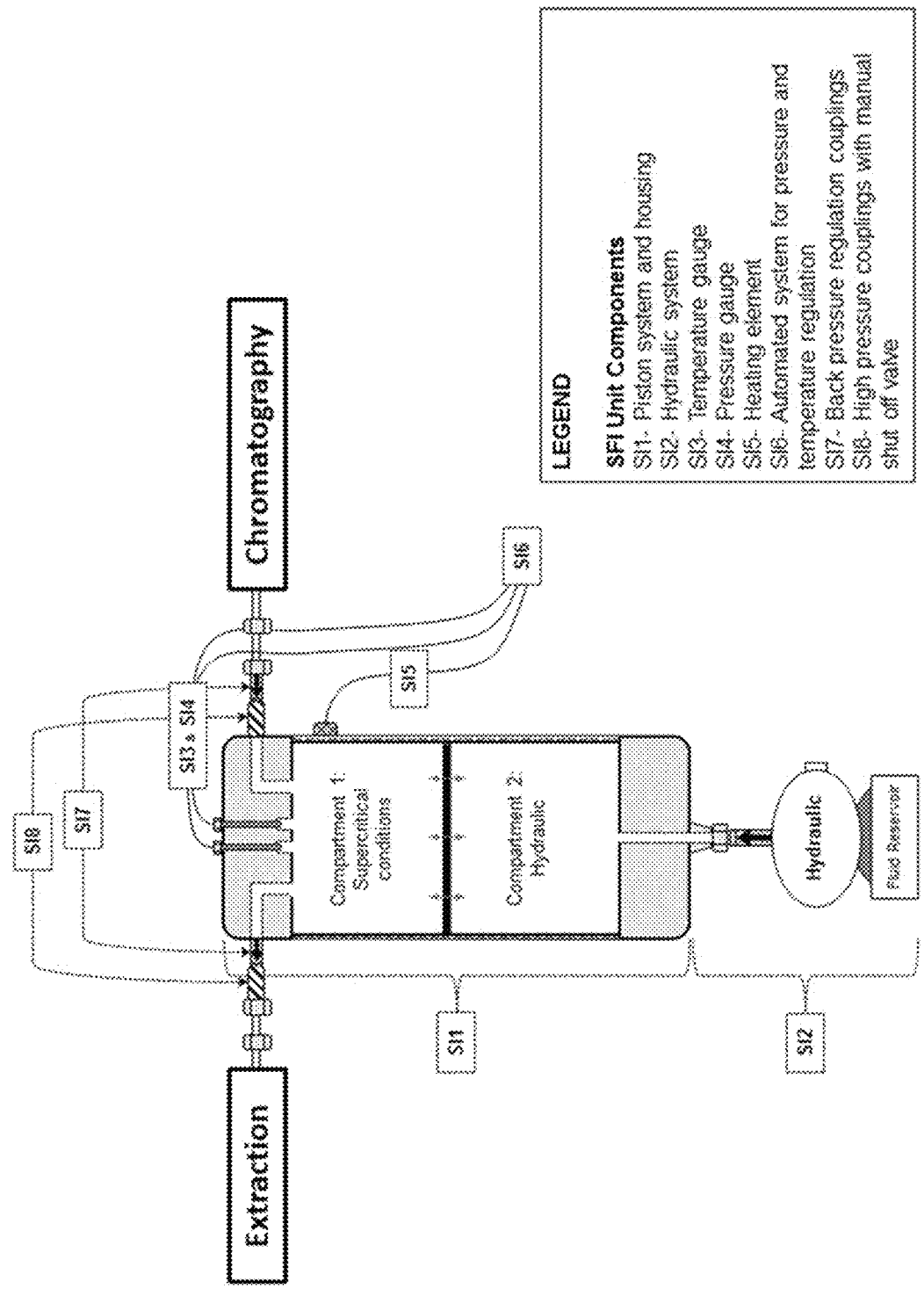
FIG. 1 shows, according to some embodiments, a schematic diagram of an exemplary dynamic interface system, especially a Supercritical Fluid Interface (SFI) positioned between an extraction device and a chromatographic purification device, wherein the following numeral and/or alphabetical symbols representing relevant parts as follows:
SI1—Piston system and housing
SI2—Hydraulic system
SI3—Temperature gauge
SI4—Pressure gauge
SI5—Heating element
SI6—Automated system for pressure and temperature regulation (Controller)
SI7—Backpressure regulation coupling
SI8—High pressure coupling with manual shut off valve.
Figure 2:
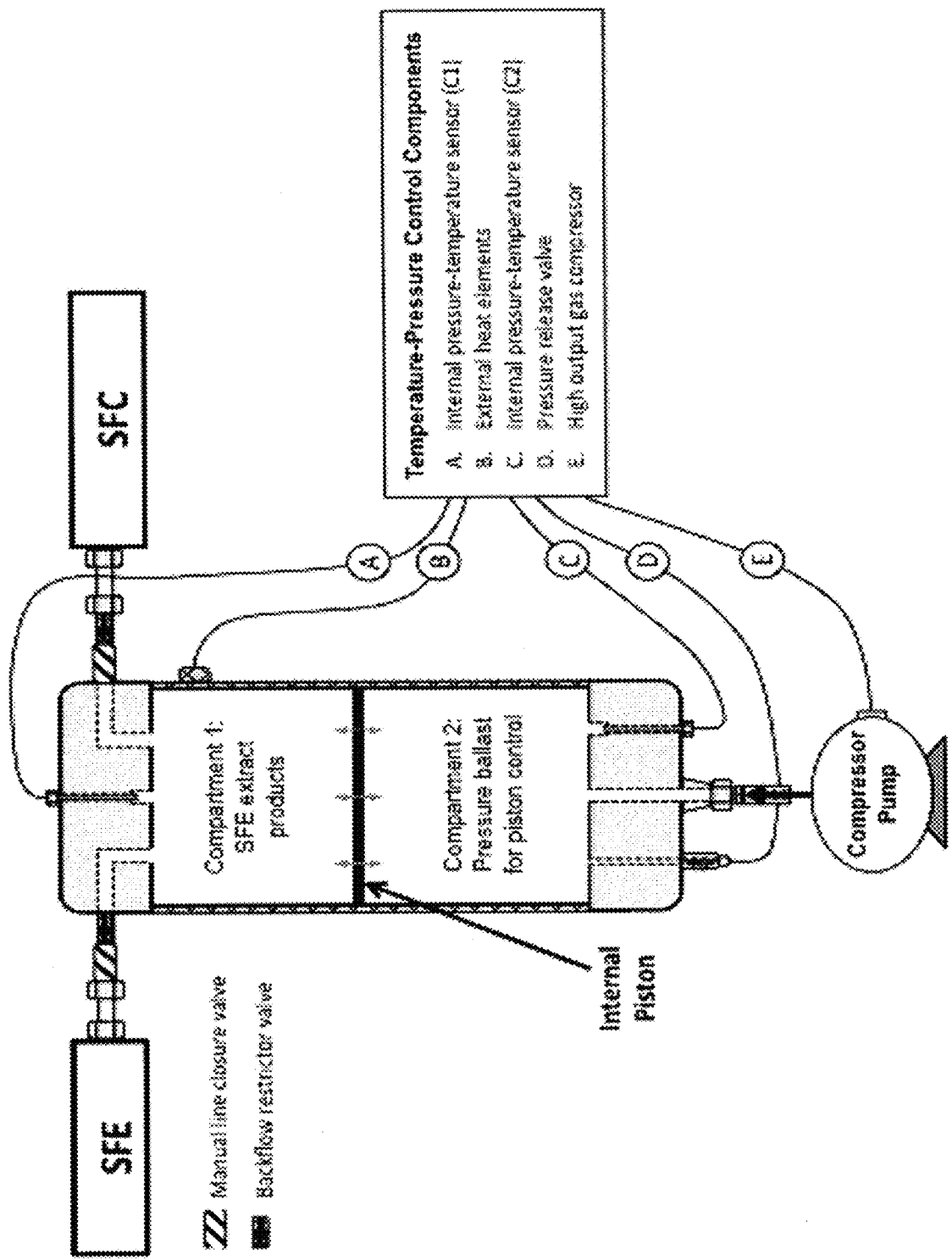
FIG. 2 shows, according to some embodiments, a schematic diagram of an exemplary Supercritical Fluid Interface (SFI) positioned between a Supercritical Fluid Extraction device (SFE) and a Supercritical Fluid chromatographic device (SFC), wherein the following numeral and/or alphabetical symbols representing relevant parts as follows:
A. Internal pressure-temperature sensor (C1)
B. External heat elements
C. Internal pressure-temperature sensor (C2)
D. Pressure release valve
E. High output gas compressor.
Figure 3:
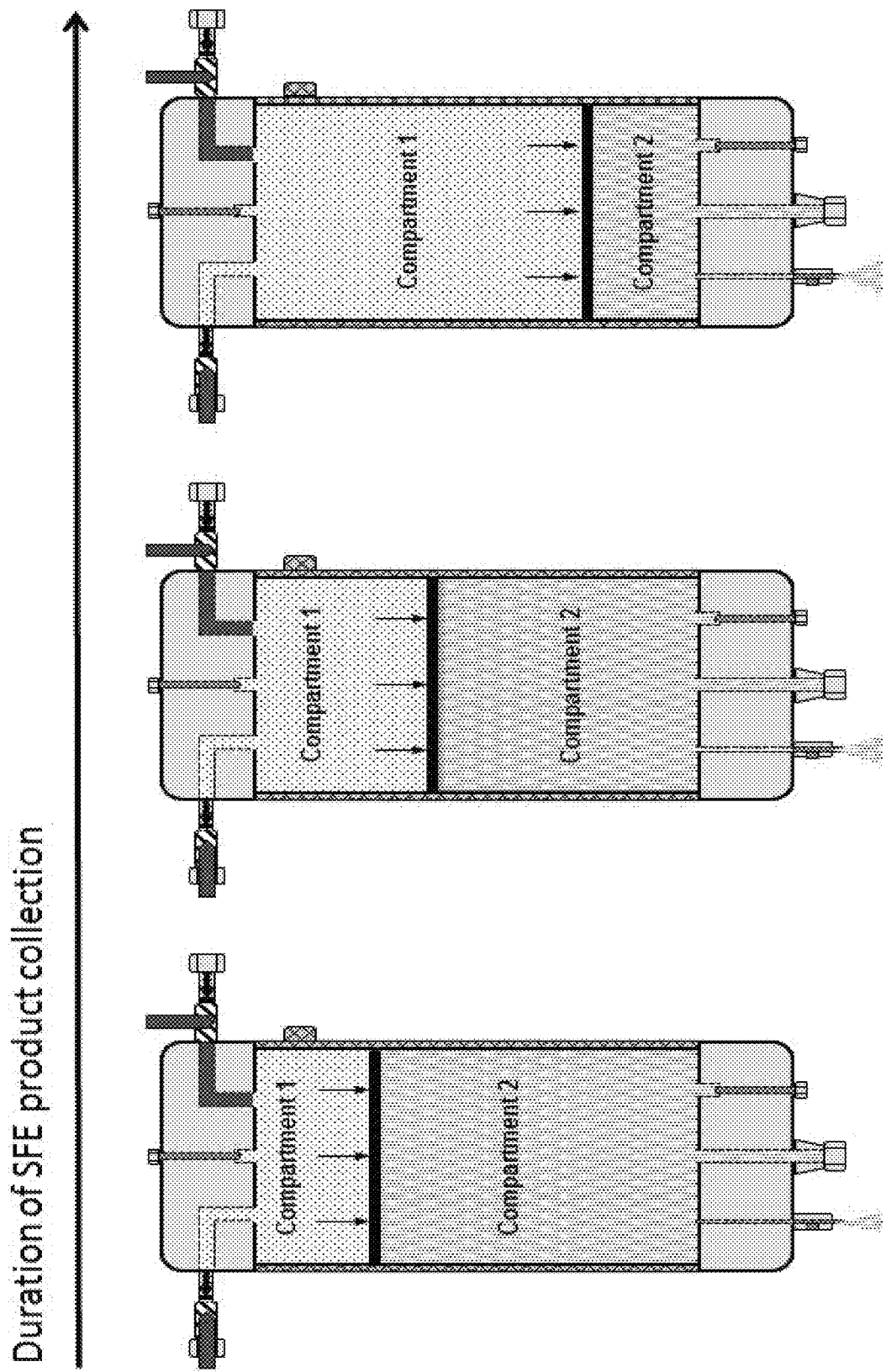
FIG. 3 shows an exemplary representation of the Supercritical Fluid Interface (SFI) collecting products from a Supercritical Fluid Extraction (SFE) device, according to some embodiments, wherein the valve connecting with the Super Fluid Chromatography (SFC) device is closed, while the vale connecting to the SFE is opened and the volume of the compartment 1 increases, while the volume of the compartment 2 decreases.
Figure 4:
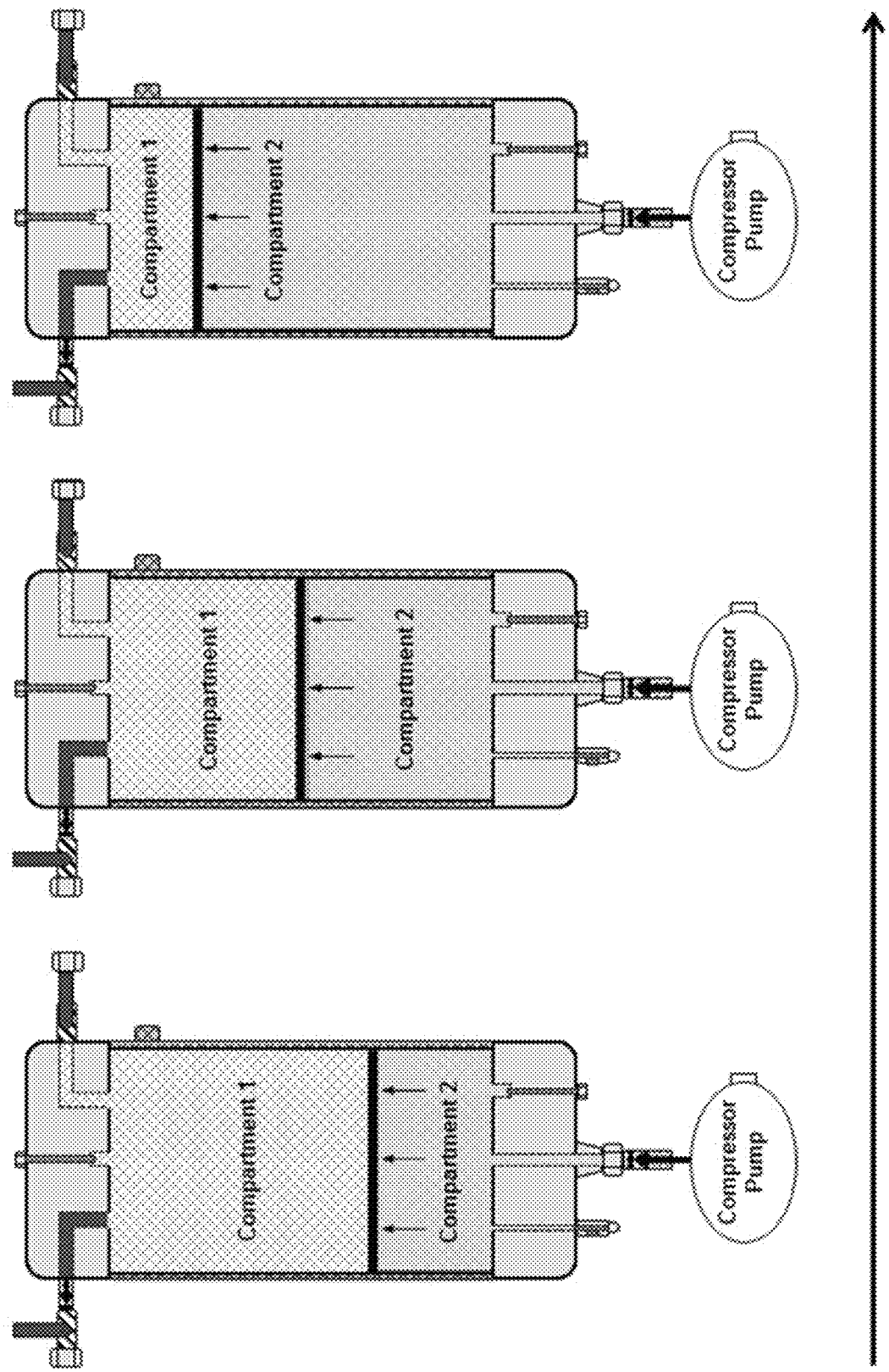
FIG. 4 shows an exemplary representation of the Supercritical Fluid Interface (SFI) injecting products to the Super Fluid Chromatography (SFC) device, according to some embodiments, wherein the valve connecting with the Super Fluid Extraction (SFE) device is closed, while the vale connecting to the SFC is opened and the volume of the compartment 1 decreases, while the volume of the compartment 2 increases under the pressure from the compressor pump.

As shown in FIG. 1, a Supercritical Fluid Interface (SFI) is an embodiment of a dynamic interface system that is positioned between an extraction device and a chromatographic purification device. The Supercritical Fluid Interface is designed to capture extracted solutions discharged from extraction technologies that are pressure and temperature dependent, and hold extracted solutions in stasis ready for injection into chromatography technologies. The SFI is designed as a piston driven chamber using the volume to control pressure, see SI1. FIG. 2 is a Supercritical Fluid Interface coupling supercritical fluid extraction (SFE) with supercritical fluid chromatography (SFC). FIG. 3 and FIG. 4 illustrate how the piston works to control pressure during extract capture and during chromatography injections.

SFI piston can be driven by a variety of mechanisms; a mechanical force, pneumatic force, hydraulic force, assuming the seals surrounding the piston are able to contain the supercritical solution within the SFI chamber and not transfer undesired material into the SFI chamber during expansion and compression to the piston. The function of the piston in the chamber of the SFI is to retract to increase volume within the SFI collection chamber as it collects supercritical solution from the SFE machine (see FIG. 3), and to compress there for reducing volume to inject the SFC column with metered boluses of supercritical solution (see FIG. 4).

Compressor Pump Activation and SFC Input $CO_2$ reaches a supercritical state at minima temperature-pressure conditions of 31.1° C. and 1070.4 psi (73.8 bar). However, SFE and SFC operations can exceed temperature-pressure ranges of 100° C. and 10,000 psi (689.5 bar). Therefore, the proposed interface bladder device embodies a flexible platform design and interchangeable component assembly to accommodate coupling of SFE and SFC instruments with operational ranges between 31.1-100° C. and 1070.4-10,000 psi (73.8-689.5 bar).

All structural components are stainless steel (316), high strength aluminum, or other materials capable of withstanding repeated exposure to temperature-pressure limits (above), environmental corrosion, and dissolution by supercritical carbon dioxide. Gasket components are Buna 90 or other materials with similar properties.

Temperature will be monitored and controlled by electronic systems with physical components for heating-cooling consisting of a combination of circulating water or air, electric heating elements, and/or passive insulation materials (e.g. solid foams, metallic films, fiber fillers, etc.). Functional range of all temperature control components must match the specifications of the SFE and SFC processes (above). Location of the pressure-temperature monitoring and control components are shown on the diagram (components A-C). Monitoring and adjustment of the control systems can be accomplished manually or with computerized systems.

Figure 5:
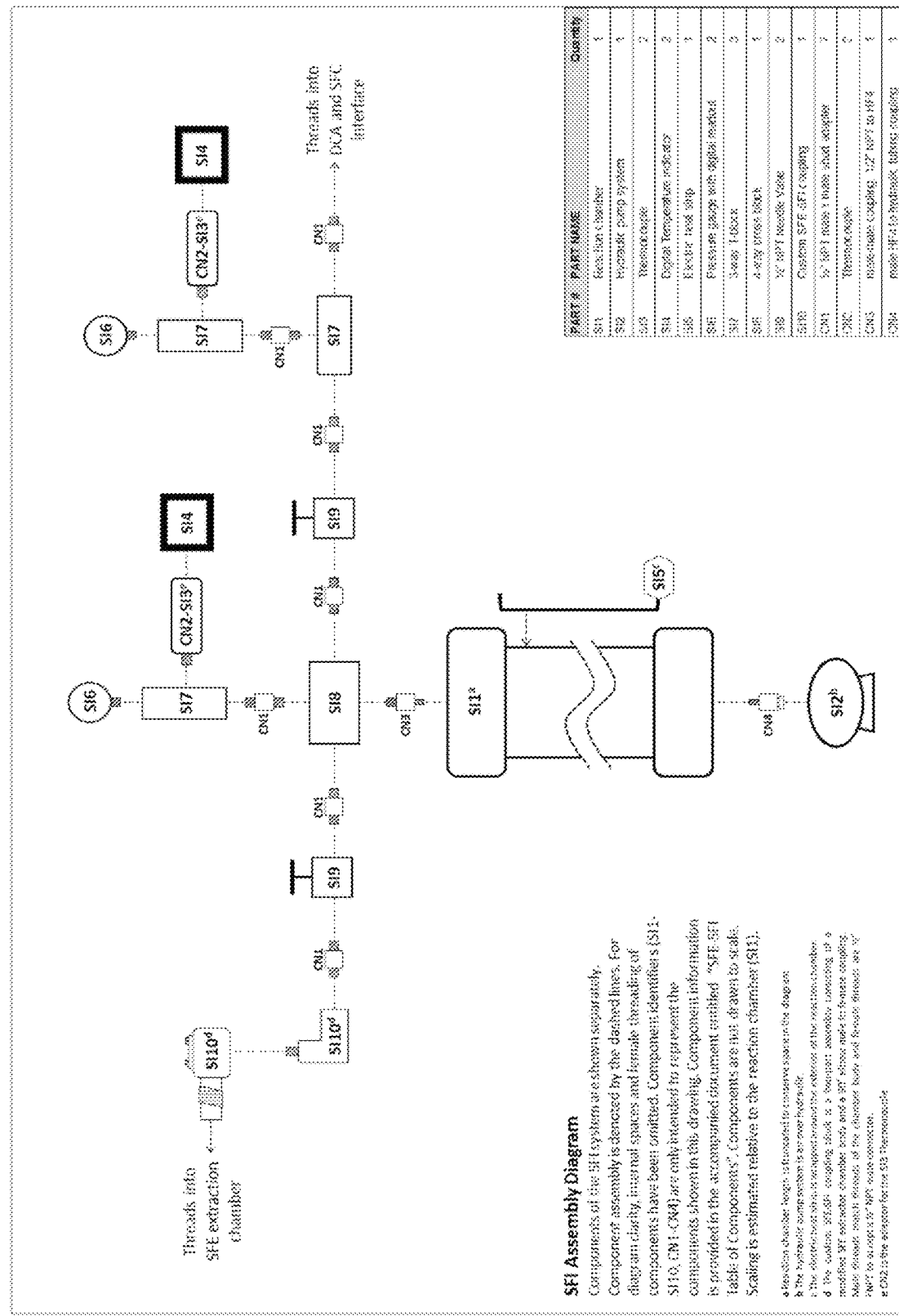
FIG. 5 shows, according to some embodiments, a schematic assembly diagram of an exemplary Supercritical Fluid Interface (SFI), wherein the following numeral and/or alphabetical symbols representing relevant parts as follows:
SI1—Reaction chamber
SI2—Hydraulic pump system
SI3—Themo-couple
SI4—Digital Temperature Indicator
SI5—Electric heat strip
SI6—Pressure gauge with digital readout
SI7—3-way T-block
SI8—4-way cross block
SI9—½" NPT needle valve
SI10—Custom SFE-SFI coupling
CN1—½" NPT male×male short adapter
CN2—Thermo-couple
CN3—Male-male coupling, ½" NPT to HF4
CN4—Male HF4 to hydraulic tubing coupling.

FIG. 5 is the assembly diagram of an example of the SFI. It lists all of the components and shows how they articulate. This diagram includes a data collection apparatus used for validation experiments.

The Supercritical Fluid Interface, is a novel technology designed to directly couple SFE with SFC and eliminate the depressurization-dissolution-repressurization steps currently required for the transition between these two technologies. Dynamic flexibility of the SFI platform allows for the coupling of commercially available SFE and SFC instruments in a continuous arrangement. We have found that this interface would accommodate different solvents and phases and can be tooled to articulate alternate extraction and chromatography technologies.

The Supercritical Fluid Interface serves two basic functions. First, it collects and holds extract-laden SFE products in a solubilized supercritical state. Second, it serves as an injection device allowing for metered introductions of the SFE products into an SFC instrument.

The following basic overview on supercritical fluid technology will assist in understanding how and why our SFI invention provides a new, meaningful coupling between SFE and SFC devices:

A supercritical fluid is any substance at a temperature and pressure above its critical point, where distinct liquid and gas phases do not exist. It can effuse through solids like a gas, and dissolve materials like a liquid.

Supercritical Fluid Extraction is the process of separating one component (the extractant) from another (the matrix) using supercritical fluids, at certain temperatures and pressures, as the extracting solvent. Extraction is usually from a solid matrix (like plant material) but can also be from liquids. SFE is used on a large scale to either strip unwanted material from a product (e.g. decaffeination) or collect a desired product (e.g. essential oils). Carbon dioxide ("$CO_2$") is the most used supercritical fluid, sometimes modified by co-solvents such as ethanol or methanol.

The SFI prototype was assembled by Cornerstone Technologies. The chamber used was a TOC piston reaction chamber provided by High Pressure Inc. Each component was independently pressure tested and assembled and pressured tested to 5000 psi by High Pressure Inc. prior to shipping.

The SFE was provided by OCO Labs Super C supercritical $CO_2$ fluid extraction benchtop machine.

The SFI was pressure tested by Cornerstone Technologies using $CO_2$ up to 3000 psi. Cornerstone Technologies achieved Supercritical state using $CO^2$, the supercritical state was held for 4 hours without manipulation of the SFI or the addition of supplemental $CO_2$. We then tested pressure with liquid, using water, and with gas using $CO_2$ in subcritical and gaseous states, we held both in stasis, +/−50 psi, for 8 hours.

After testing differing pressure and temperature combinations, and changing pressures and temperatures dynamically, we are confident that the SFI is capable of dynamically coupling gas, liquid, Supercritical oil extraction technologies to gas, liquid, and supercritical chromatography technologies.

Cannabinoid compounds can be extracted from raw *cannabis* plant material using a variety of methods to produce *cannabis* oils, which are crude mixtures of cannabinoids and may include a number of additional phytocompounds. The respective cannabinoid concentrations contained in these oils are highly dependent upon the starting plant material. For example, production of oils with high THC content begins with high THC containing plant material, while production of oils with high CBD content begins with low THC and high CBD containing plant material. Subsequently, the choice of starting plant material provides a rudimentary method for determining cannabinoid compounds contained in the extract products.

Most cannabinoids are carbon-hydrogen rich, chemically uncharged, lipophilic, and readily soluble in non-polar organic solvents. Subsequently, extraction methods based on simple organic solvation techniques exploit these chemical properties to draw cannabinoids out of plant materials. A generic extraction protocol consists of steps in which finely ground plant material is saturated with organic solvents to form a slurry. Organic solvents are typically non-polar liquids such as hexane, ether, chloroform, acetonitrile, benzene, and/or ethanol combined in different ratios with water (Gil-Chavez et al. 2013). With time and agitation, non-polar cannabinoids are drawn out of the plant material and into the solvent. The resultant slurry is filtered to remove plant material and isolate the solvent, which is then evaporated to yield *cannabis* extracts.

One application of the SFI in connection with SFE and SFC is for extraction and isolation of *cannabis* compounds using supercritical $CO_2$ and/or other co-solvents.

Organic solvent extraction methods are highly efficient and often used for analytical determination of cannabinoid content in plant material. For example, two-phase solvent extraction methods coupled with centrifugal partition chromatography were used to isolate and purify >90% of several cannabinoids including THC, THCA, CBD, CBDA, CBG, CBGA, and CBN from *cannabis* material. However, there are several limitations to organic solvent extractions.

SFE-$CO_2$ methods have been shown to extract major cannabinoids with relatively good precision due to the solubilities of cannabinoids in SC—$CO_2$. Experimental data indicate solubility of delta-9-tetrahydrocannabinol (THC) in SC—$CO_2$ at pressures of 220-240 bar exhibits a two-fold increase as temperature is raised from 42° C. to 72° C. (Perrotin-Brunel et al. 2010). In contrast, the molar solubility of cannabinol (CBN) in SC—$CO_2$ follows an inverted-U curve across these temperature ranges, but at lower pressures 160-180 bar, CBN solubility at 54° C. is two-fold greater than that observed at 41° C. or 61° C. (Perrotin-Brunel et al. 2010). Therefore, it is possible to employ a range of pressure and temperature conditions to extract cannabinoid compounds with SFE-$CO_2$ technologies.

Cannabinoids are chemically similar compounds and nonpolar solvents indiscriminately extract all cannabinoids contained within the plant material. Thus, additional processes, such as chromatography, are needed to isolate specific cannabinoid compounds. Additionally, most organic solvents are volatile compounds and classified as hazardous materials. Purchase, transport, and disposal are subject to regulation, licensing, and fees. Large-scale extraction operations will undoubtedly incur numerous indirect costs associated with the use of these solvents. There are also consumer concerns about residual solvent contamination of extract products. Because of the drawbacks associated with organic solvent extractions, especially with products destined for human consumption, methods for producing *cannabis* extracts have shifted toward use of supercritical carbon dioxide (SC—$CO_2$).

The Process and SFI Function

The following is an example of a cannabinoid extraction and refining process using the SFI in-line with an SFE and SFC.

Preparing Hemp Plant Material.

1. Plant material should be dried. Plant material may be placed in a dehydrator or an oven at low temps (under 110° F.) and dehydrated to 90%.
2. Plant material needs to be grounded; the size should be similar to coarse ground coffee. We have used a commercial food processor to achieve this.
3. Grounded plant material needs to go through a decarboxylation process. We have used thermal decarboxylation. The ground plant material is placed in an airtight oven safe container and baked in an oven for 60 minutes at 160° F.

Equipment

Oven, Grinder (commercial food processor), air tight sealed oven safe container.

Extraction

There are two supercritical extraction techniques we use. The first being selective, and second is gradient. A selective extraction uses one pressure and temp throughout the entire run. Selective extractions concentrate on a single fraction, extracting all of the selected fraction but leaving other non-selected oil fractions on the plant. This extraction process is ideal when you are trying to increase a fractions percentage within whole oils or when you are trying to reduce the presence of an undesired fraction within the extracted oil. The second process is gradient. The gradient method uses increasing pressures and temperatures through the extraction process. By starting low and gradually increasing pressures and temperatures from sub-critical to maximum supercritical you can extract all oil fractions and terpenes. The gradient process is ideal for our configuration, as it captures the largest quantity of oil.

Gradient Extraction Process

1. Prepared plant material was packed into extraction chambers, 1 oz plant material to 1 liter of volume.
2. The extraction chamber is secured to supercritical fluid extraction equipment (SFE) and the extraction chamber is heated to first operating temp, and heat soaked for 20 minutes.
3. The valve between the SFE and the supercritical fluid interface (SFI) is opened where the valve between the SFI and the SFC are closed.
4. The SFE extraction cylinder is then filled with gaseous $CO_2$, then the pumps are turned on until the first subcritical pressure is reached in both the SFE and SFI. Subcritical extraction 1400-2000 PSI is used to capture tannins and terpenes.
5. Once the desired pressure and temp are achieved, water is slowly released from the hydraulic side of the SFI increasing volume in the supercritical side of the SFI. The extract in supercritical fluid solution being produced by the SFE will be captured and held within the SFI. It is imperative that the pressure and temperature in the SFI remains consistent with the temperature and pressure in the SFE during the extraction process.
6. After the selected time frame for subcritical extraction is met, the valve between the SFE and the SFI is closed. The SFE continues to run, building pressure to the next designated pressure and any adjustments in temperature can be made during this time. Simultaneously, the SFI will be injecting the contents into the solvent transfer module, or chromatography equipment. The pressure generator should be used to control the SFI to SFC injection and to keep fluid moving into the hydraulic side of the SFI.
7. After the SFI injects the solution captured during the extraction, the valve between the SFI and SFC will be closed, the hydraulic valve should be left opened and the pressure generator should be used to fill the hydraulic side of the SFI.
8. To fill the SFI, the pressure generator will need to be refilled several times. This is done by closing the valve between the SFI and the Pressure generator, then opening the valve between the pressure generator and the hydraulic fluid reservoir. The pressure generator control wheel is turned to draw hydraulic fluid into the pressure generator. The valve is closed between the hydraulic fluid reservoir and the pressure generator. The valve between the pressure generator and the SFI is opened, and the pressure generator control wheel is turned to inject the hydraulic fluid into the hydraulic side of the SFI. This process will be repeated until the hydraulic side of the SFI is completely filled.
9. After the hydraulic side of the SFI is completely filled the valve from the SFI and the hydraulic pressure generator should remain open, while the valve between the pressure generator and the hydraulic reservoir should be closed.
10. Next, the valve between the SFE and the SFI will be opened. The pressure will build within the SFE and SFI together until it has reached the correct pressure and temperature for the next run.
11. Once the pressure and temperatures are met within the SFE and SFI, the next extraction can begin. Steps 5-11 are repeated. This process will be repeated every pressure and temp designated for the gradient extraction.

Selective Extraction

For selective extraction follow steps 1-9 should be followed once per extraction.

Chromatography

SFI to SFC attachment is direct and no special considerations need to be taken from SFI to SFC. The articulating couple will attach the SFI at the discharge port on the cross block valve on the supercritical side and the blending unit of the SFC. Injections into the blending unit from the SFI will mimic the injection from the blending unit into the SFC both in volume and rate.

Injection rate and volume from the SFI into the SFC will be determined by chromatography instruments and methods.

Chromatography and fraction collection will be performed in accordance with our developed method.

Equipment

SFE, SFI, SFC

In summary, the Supercritical Fluid Interface ("SFI") is a novel technology designed to provide a dynamic inline interface between Supercritical Fluid Extraction ("SFE"), and Supercritical Fluid Chromatography ("SFC"). The SFI is capable of interfacing; gas, subcritical and supercritical fluid extraction methods and pair with gas, subcritical and supercritical fluid chromatography technologies that operate within the pressure and temperature parameters of the SFI. The SFI prototype built by Cornerstone Technologies is designed to operate up to 200 degrees celsius and 5000 psi. Extraction and chromatography technologies that can articulate with the SFI would use a gas, sub/supercritical fluid solvent, and perform extraction and chromatographic separation between; atmospheric to 5000 psi, ambient temperature to 200 degrees celsius. This interface technology allows for an inline oil extraction and chromatographic separation, the SFI can pair extraction and chromatography with the same solvent in different mobile phases, whereas the extraction can be performed using $CO_2$ as a solvent in sub-critical phase and the SFI can receive the subcritical solution and then increase pressure and/or temperature to achieve supercritical state as required for injection into supercritical fluid chromatography technologies. The SFI was conceived for a direct dynamic coupling between SFE and SFC to extract and refine cannabinoids from the *cannabis* industrious, hemp, plant. Albeit a very useful technology for streamlining extraction and refinement of cannabinoids it is not limited to this industry. The SFI can be used to improve efficiency in an industry that extracts and refines oils, through chromatography, from organic materials using a gas, or sub/supercritical fluid as a solvent and mobile phase.

INDUSTRY APPLICATIONS

The dynamic interface system and method of the present invention can be used to isolate and purify >90% of several cannabinoids including THC, THCA, CBD, CBDA, CBG, CBGA, and CBN from *cannabis* material.

The dynamic interface system and method of the present invention additionally may be used for obtain other purified compounds from mixture sources and may be used in food processing, cosmetic, pharmaceutical, agricultural and other fields for extraction, separation, fractionation, micronization, and encapsulation of bioactive compounds for food, pharmaceutical, cosmetic and other applications.

For example, the dynamic interface system and method of the present invention can be used for coffee and tea decaffeination, nicotine extraction, hops extraction, spices/flavors/aromas/color extraction, deasphalting petroleum fractions, recovery and purification of lube oils, coal liquefaction, chemical separations and purification, polymer processing, supercritical crystallization and supercritical drying, impregnation, pollution abatement, biological applications and other fields.

The invention claimed is:

1. A dynamic interface system between an extraction device and a chromatographic purification device, comprising:

a container having an inlet and an outlet, wherein the inlet connects with the extraction device and the outlet connects with the chromatography device;
a piston in the container and dividing the container into a first compartment and a second compartment;
a pressure adjustment device in connection with the container; and
a temperature adjustment device in connection with the container.

2. The dynamic interface system according to claim 1, further comprising a temperature sensor and a pressure sensor in connection with the container.

3. The dynamic interface system according to claim 1, wherein the inlet and the outlet connect with the first compartment of the container.

4. The dynamic interface system according to claim 3, further comprising valves for opening or closing the inlet and the outlet.

5. The dynamic interface system according to claim 1, wherein the pressure adjustment device communicates with the second compartment of the container to increase or decrease the pressure in the second compartment.

6. The dynamic interface system according to claim 5, wherein the pressure adjustment device is a compressor pump.

7. The dynamic interface system according to claim 1, further comprising a control device to control opening and closing of the inlet, the outlet and the temperature and pressure.

8. The dynamic interface system according to claim 1, wherein the extraction device is a supercritical fluid extraction device and the chromatographic purification device is a supercritical fluid chromatography device; and wherein carbon dioxide is used as a solvent.

9. A separation and purification system comprising:

an extraction device;
a chromatographic purification device; and
a dynamic interface system between the extraction device and the chromatographic purification device, comprising:
a container having an inlet and an outlet, wherein the inlet connects with the extraction device and the outlet connects with the chromatography device;
a piston in the container and dividing the container into a first compartment and a second compartment;
a pressure adjustment device in connection with the container; and
a temperature adjustment device in connection with the container.

10. The dynamic interface system according to claim 1, further comprising a temperature sensor and a pressure sensor in connection with the container.

11. The dynamic interface system according to claim 1, wherein the inlet and the outlet connect with the first compartment of the container.

12. The dynamic interface system according to claim 1, wherein the pressure adjustment device communicates with the container to increase or decrease the pressure.

13. The separation and purification according to claim 9, wherein the extraction device is a supercritical fluid extraction device and the chromatographic purification device is a supercritical fluid chromatography device.

14. The separation and purification system according to claim 13, wherein carbon dioxide is used as a solvent.

15. A separation and purification method for separating at least one substance from a mixture or matrix comprising the steps of:

(a) treating the mixture or matrix with a solvent under a first pressure and a first temperature in an extraction device;
(b) outputting the mixture treated by the extraction device to an interface system under a second pressure and a second temperature;
(c) outputting the mixture of the interface system to a chromatographic purification device under a third pressure and a third temperature, where the substance is being separated; and
(d) collecting the separated substance;
wherein the interface system is connected with and located between the extraction device and the chromatographic purification device.

16. The separation and purification method according to claim 15, wherein the first pressure equals to the second pressure; and the first temperature equals to the second temperature.

17. The separation and purification method according to claim 15, wherein solvent is a liquid solvent, a gaseous solvent, a subcritical fluid solvent or a supercritical fluid solvent.

18. The separation and purification method according to claim 15, wherein the solvent is carbon dioxide and the first, second and third temperatures and pressures are such that the carbon dioxide is kept at a super critical state; and wherein the extraction device is a super critical fluid extraction device and the chromatographic purification device is a super critical fluid chromatography device.

19. The separation and purification method according to claim 18, wherein the first, second and third temperatures are 31.1-100° C. and the first, second and third pressures are 1070.4-10,000 psi.

20. The separation and purification method according to claim 15, wherein the mixture or matrix is cannabis plant material and the substance is selected from the group of delta-9-tetrahydrocannabinol (THC), tetrahydrocannabinolic acid (THCA), cannabidiol (CBD), cannabinol (CBN), cannabidiolic acid (CBNA), cannabigerol (CBG) and cannabigerolic acid (CBGA).

21. The separation and purification method according to claim 15, wherein the interface system is a container comprising:
an inlet and an outlet, wherein the inlet connects with the extraction device and the outlet connects with the chromatographic purification device;
a piston in the container and dividing the container into a first compartment and a second compartment;
a pressure adjustment device in connection with the container; and
a temperature adjustment device in connection with the container.

22. The separation and purification method according to claim 20, wherein the extraction device is a supercritical fluid extraction device and the chromatographic purification device is a supercritical fluid chromatography device.

23. The separation and purification method according to claim 20, wherein step (b) comprises the following sub-steps:
(b1) closing the outlet of the interface system to the chromatographic purification device; and
(b2) opening the inlet of the interface system to receive the mixture treated by the extraction device, and
wherein step (c) comprises the following sub-steps:
(c1) closing the inlet of the interface system to receive the mixture treated by the extraction device; and
(c2) opening the outlet of the interface system to the chromatographic purification device.

* * * * *